United States Patent
Teschner et al.

(10) Patent No.: US 7,896,814 B2
(45) Date of Patent: Mar. 1, 2011

(54) PROCESS AND DEVICE FOR LUNG VENTILATION

(75) Inventors: Eckhard Teschner, Luebeck (DE); Dieter Weismann, Gross Groenau (DE)

(73) Assignee: Dräger Medical GmbH, Lübeck (DE)

( * ) Notice: Subject to any disclaimer, the term of this patent is extended or adjusted under 35 U.S.C. 154(b) by 1049 days.

(21) Appl. No.: 11/675,800

(22) Filed: Feb. 16, 2007

(65) Prior Publication Data
US 2007/0246046 A1 Oct. 25, 2007

(30) Foreign Application Priority Data
Apr. 19, 2006 (DE) ........................ 10 2006 018 198

(51) Int. Cl.
*A61B 5/085* (2006.01)
(52) U.S. Cl. ........................ 600/529; 600/547
(58) Field of Classification Search ............... 600/529, 600/532, 536, 547; 128/204.18–204.23
See application file for complete search history.

(56) References Cited
PUBLICATIONS

Squadrone et al., Continuous Positive Airway Pressure for Treatment of Postoperative Hypoxemia, JAMA, Feb. 2, 2005, vol. 293, No. 5, pp. 589-595, American Medical Association.

*Primary Examiner*—John P Lacyk
*Assistant Examiner*—Jeffrey Choi
(74) *Attorney, Agent, or Firm*—McGlew & Tuttle, P.C.

(57) ABSTRACT

An electro-impedance tomography (EIT) system (2), with a computing unit (4) and a respirator (1) is described for gentle mechanical lung ventilation especially in case of atelectases. The presence, the extent and/or the spatial distribution of atelectases is detected by the EIT system (2) and sent to the respirator (1) so that the respiration pressure is increased step by step by the respirator (1) until the current image of the lung status corresponds to a first status image of healthy lungs or comes close to it with minimal deviations. The respiration pressure is subsequently reduced again step by step by the respirator (1) until the computing unit (4) detects a reduction of the ventilated lung areas and the respiration pressure is subsequently increased again by means of the respirator (1) to the last value at which no change occurred in the ventilated lung areas.

8 Claims, 1 Drawing Sheet

PROCESS AND DEVICE FOR LUNG VENTILATION

CROSS REFERENCE TO RELATED APPLICATIONS

This application claims the benefit of priority under 35 U.S.C. §119 of German Patent Application DE 10 2006 018 198.0 filed Apr. 19, 2006, the entire contents of which are incorporated herein by reference.

FIELD OF THE INVENTION

The present invention pertains to a process and a device for lung ventilation (also known as lung respiration).

BACKGROUND OF THE INVENTION

Electric impedance tomography (EIT) is a process, which is known per se, in which the electric impedance between the feed point and the test point can be calculated by feeding an alternating electric current of, e.g., 5 $mA_{eff}$ at 50 kHz into any electrically conductive body, here preferably into the human body, and measuring the surface potentials resulting therefrom at different points of the body. A two-dimensional tomogram of the electric impedance distribution in the body being considered can be determined on the basis of suitable mathematical reconstruction algorithms by gradually rotating the current feed sites around the body while measuring at the same time the surface potentials along a section plane.

Such a tomograph of the impedance distribution of the human body is of interest in medicine because the electric impedance changes both with the air content and the extracellular fluid content in the tissue. It is thus possible to visualize and monitor with this process especially the ventilation, i.e., the ventilation of the lungs, as well as the changes in the end-expiratory lung volume in a regionally resolved manner.

It is known that ventilated lung areas as well as the changes therein over time can be represented by means of EIT.

It was reported that the recovery from abdominal surgical procedures normally takes place rapidly and without complications (Squadrone et al., Continuous Positive Airway Pressure for Treatment of Postoperative Hypoxemia in *JAMA*, Feb. 2, 2005, Vol. 293, No. 5, pp. 589-595), but 30% to 50% of the patients nevertheless develop postoperative hypoxemia as a consequence of the development of atelectasis, this happening even in patients in whom no postoperative complications developed. Even though the administration of oxygen and breathing training can be employed highly efficiently in most cases, respiratory failure may develop during the early postoperative phase, which calls for endotracheal intubation and mechanical ventilation in 8% to 10% of this patient group, which may in turn lead to complications in the hospital. It is therefore important to recognize a change in the lung status as early as possible and to set the respirator (ventilator) such that exacerbation of the patient's condition is counteracted in time.

This is especially true in connection with surgical procedures during which atelectases frequently develop.

SUMMARY OF THE INVENTION

The object of the present invention is therefore to provide an improved process and a device for lung ventilation, which detect and quantify the development of atelectasis and operate a respirator such that the atelectases are extensively eliminated.

According to the invention, a process is provided for lung ventilation by means of a combination of an EIT system, a computing unit and a respirator. A first status image of the healthy lungs is first recorded prior to anesthetization by means of the EIT system and the total area and/or the distribution in space of ventilated lung areas are determined from the image values by means of the computing unit. Second or additional status images are recorded after assumed lung damage and the total area and/or the spacial distribution of ventilated lung areas are determined. The total areas and/or the distribution in space of the ventilated lung areas from the first and second or further status images are compared by means of the computing unit and are analyzed for the presence of lung areas that have no or reduced ventilation due to atelectases. The information on the presence, the extent and/or the distribution in space of atelectases is sent by the EIT system to the respirator so that the respiration pressure is increased step by step by means of the respirator as a function of the status image or the currently determined status images until the current image of the lung status corresponds to the first status image or comes close to it with minimal deviations. The respiration pressure is subsequently reduced again step by step by the respirator until the computing unit detects a reduction of the ventilated lung areas and the respiration pressure is subsequently increased again by means of the respirator to the last value at which no change occurred in the ventilated lung areas.

The stepwise increase in the respiration pressure may be carried out in such a way that the amount of the increase is continuously decreased.

After a comparison of the first image of the lung status with the second and subsequent images of the lung status and after comparison with reference values stored in the computing unit, termination signals may be sent to the respirator for changing the respiration pressures step by step.

The respiration pressure may be increased or decreased by means of the respiration volume applied by the respirator.

According to another aspect of the invention, a device is provided for lung ventilation by means of a combination of an EIT system, a computing unit and a respirator. The EIT system is set up to record a first image of the lung status and a second or additional images of the lung status subsequent to one another over time from all measured impedance changes and to determine the total area and/or the distribution in space of ventilated lung areas. The respirator is set up to increase the respiration pressure or the respiration volume by signals from the EIT system step by step until the current image of the lung status corresponds to the first status image or comes close to this with minimal deviations, to subsequently reduce the respiration pressure or the respiration volume step by step until the computing unit detects a reduction of the ventilated lung areas and to subsequently increase the respiration pressure and the respiration volume again to the last value at which there was no change in the ventilated lung areas.

A special advantage of the present invention is the possibility of gently respirating the patient with improved ventilation of the lungs during and after a medical and especially surgical procedure with possible development of atelectasis.

An exemplary embodiment of the present invention will be explained below by means of the only FIGURE, which schematically shows the principal components of a device for carrying out the process for lung ventilation. The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which preferred embodiments of the invention are illustrated.

DESCRIPTION OF THE PREFERRED EMBODIMENTS

Figure 1:
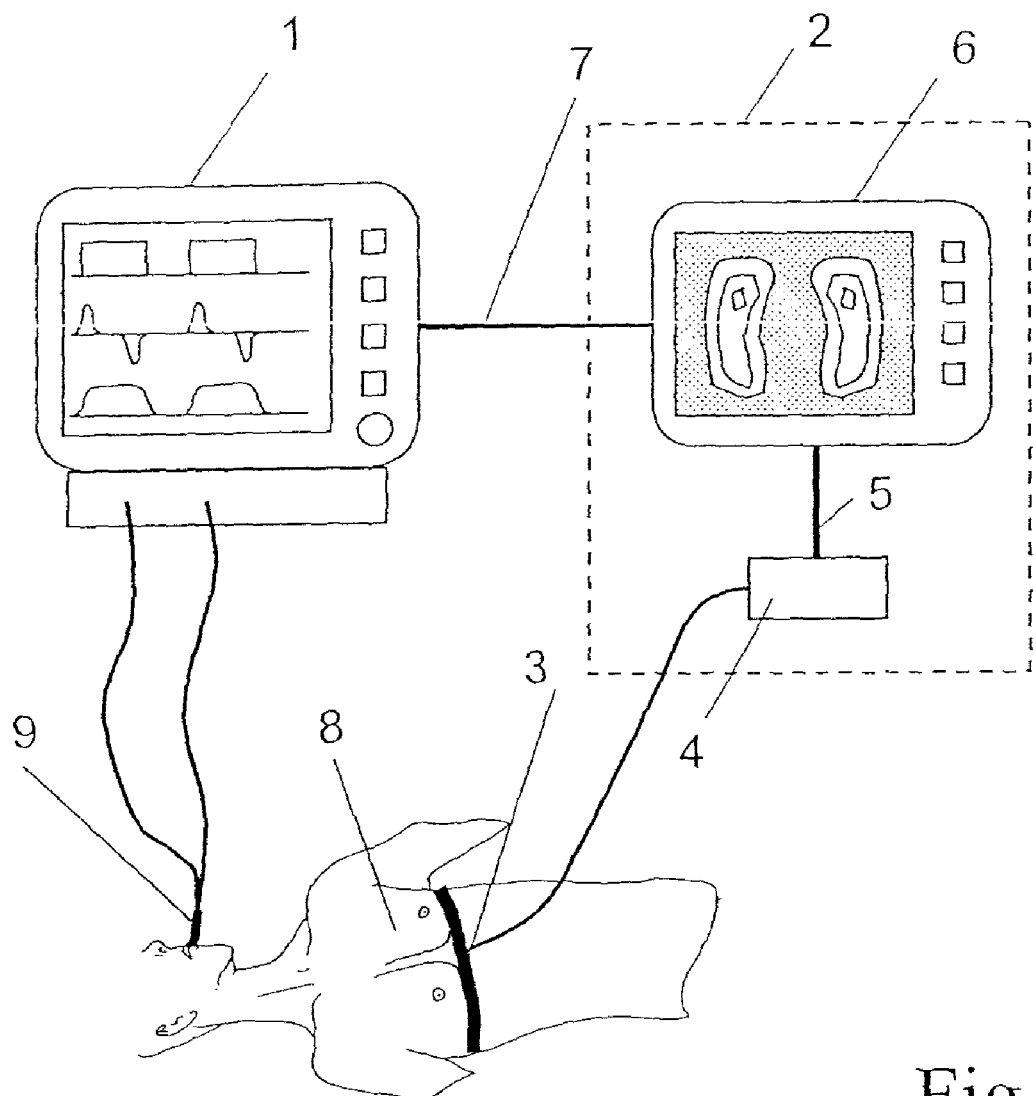
FIG. 1 is a schematic view showing a system for practicing the process according to the invention.

Referring to the drawing in particular, a first image of the lungs, which are not yet compromised by the anesthesia, is determined by means of the EIT system 2 for the patient 8, in the recumbent position, before initiation of anesthesia. The patient 8 will have to undergo, for example, major surgery.

The EIT system 2 contains, as is shown, an evaluating and display unit 6 and a computing unit 4. The system 2 detects images of the lung status of the patient 8 with the use of an electrode belt 3.

The computing unit 4 may also be arranged separately outside the EIT system 2, for example, between the evaluating and display unit 6 and the respirator 1. The computing unit 4 is connected to the evaluating and display unit 6 by means of the line 5. Furthermore, a technical alternative is that the EIT system 2 is arranged in an integrated total system together with the computing unit 4 and the respirator 1. While the electrodes remain in the same position as before, a second image and optionally additional images of the status of the possibly atelectatic lungs are determined after the initiation of anesthesia.

The EIT system 2 compares the image elements of the first status image with those of the second status image and optionally of the subsequent status images and identifies the total area and/or the spatial distribution of the areas in which deviations have occurred.

Should the comparison of the first and second status images and optionally of the subsequent status images reveal that the total area of ventilated lung areas has become smaller or the distribution of ventilation in space has changed because of atelectases that developed during the anesthesia, this information is reported to the respirator 1 connected via a bidirectional data connection 7. All status images are preferably stored in order to make it possible to retrospectively monitor and make document changes.

In response to this information, the respirator 1 adjusts the respiration settings, especially the respiration pressures and/or the tidal volumes step by step. The respiration pressure is increased step by step until the current image of the lung status corresponds to the first status image or comes close to this with minimal deviations. The information sent by the EIT system 2 can also be used as a basis for decisions on whether the respirator 1 performs a recruitment manoeuver in the patient to reopen atelectatic lung areas.

The EIT system 2 continuously compares the first status image with the subsequent status images obtained from the change in the respiration pressures and sends feedback in the sense of a control loop to the respirator 1, which performs further adjustments of the respiration setting if necessary.

After the atelectatic lung areas have been successfully reopened, the respiration pressures/the tidal volumes are again lowered step by step during the further course of this control until the computing unit 4 again recognizes a difference between the first status image and the particular current status image concerning the determined total area and/or the spatial distribution of the tidal volumes and the respiration pressures and/or the tidal volumes are then again increased to the last value at which no differences were determined.

The computing unit 4 defines all image values of both the first and second or subsequent status images, whose corresponding impedance changes exceed a certain threshold value, as ventilated lung areas and subsequently determines a value that represents the total area of the ventilated lung areas.

In addition, the spatial distribution of the ventilated lung areas is determined by means of the computing unit 4 in a number of regions of interest (ROI) of both status images.

The primary goal of this control is to obtain a particular current image of the lung status whose total area and in which the distribution of the ventilated lung areas correspond to the first status image. If a sufficient gas exchange is again able to be established after elimination of the atelectases, the patient can be started to be weaned off mechanical respiration with known methods.

While specific embodiments of the invention have been shown and described in detail to illustrate the application of the principles of the invention, it will be understood that the invention may be embodied otherwise without departing from such principles.

What is claimed is:

1. A process for lung ventilation, comprising:
providing a combination of an electric impedance tomography (EIT) system, a computing unit and a respirator;
recording a first status image of healthy lungs with the EIT system;
determining, with the computing unit, a total area and/or a spatial distribution of ventilated lung areas from image values;
recording second or additional status images after assumed lung damage and after the total area and/or the spatial distribution of ventilated lung areas are determined;
comparing, with the computing unit, the total areas and/or the spatial distribution of the ventilated lung areas from the first and second or further status images and analyzing for the presence of lung areas that have no or reduced ventilation due to atelectases;
sending information on the presence, the extent and/or the spatial distribution of atelectases by the EIT system to the respirator;
increasing the respiration pressure step by step, with the respirator, as a function of the status image or the currently determined status images until the current image of the lung status corresponds to the first status image or comes close to the first status image with minimal deviations; and
reducing the respiration pressure step by step, with the respirator, until the computing unit detects a reduction of the ventilated lung areas and subsequently increasing the respiration pressure, with the respirator, to the last value at which no change occurred in the ventilated lung areas.

2. A process in accordance with claim 1, wherein the step-by-step increase in the respiration pressure is carried out in such a way that the amount of the increase is continuously decreased.

3. A process in accordance with claim 1, wherein after comparing of the first image of the lung status with the second and subsequent images of the lung status and after comparing with reference values stored in the computing unit, termination signals are sent to the respirator for changing the respiration pressures step by step.

4. A process in accordance with claim 1, wherein the respiration pressure is increased or decreased by means of respiration volume applied by the respirator.

5. A device for lung ventilation, the device comprising:

an electric impedance tomography system for recording a first image of the lung status and for recording a second or additional images of the lung status subsequent to one another over time from measured impedance changes and to determine a total area and/or a spatial distribution of ventilated lung areas;

a computing unit;

a respirator for increasing respiration pressure or increasing respiration volume, by signals received from the electric impedance tomography system, step by step until the current image of the lung status corresponds to the first status image or comes close to the first status image with minimal deviations, and for subsequently reducing the respiration pressure or the respiration volume step by step until the computing unit detects a reduction of the ventilated lung areas and to subsequently increase the respiration pressure and the respiration volume again to the last value at which there was no change in the ventilated lung areas.

6. A device in accordance with claim 5, wherein the step-by-step increase in the respiration pressure is carried out in such a way that the amount of the increase is continuously decreased.

7. A device in accordance with claim 5, wherein after comparison of the first image of the lung status with the second and subsequent images of the lung status and after comparison with reference values stored in the computing unit, termination signals are sent to the respirator for changing the respiration pressures step by step.

8. A device in accordance with claim 5, wherein the respiration pressure is increased or decreased by means of respiration volume applied by the respirator.

* * * * *